United States Patent [19] [11] 4,420,257
Fukuda et al. [45] Dec. 13, 1983

[54] LASER LIGHT SCATTERING PHOTOMETER

[75] Inventors: Mitsutoshi Fukuda; Nobuyuki Baba; Kenji Arichika, all of Nanyo, Japan

[73] Assignee: Toyo Soda Manufacturing Co., Ltd., Yamaguchi, Japan

[21] Appl. No.: 121,314

[22] Filed: Feb. 14, 1980

[51] Int. Cl.³ .......................................... G01N 21/00
[52] U.S. Cl. ................................... 356/341; 356/343
[58] Field of Search ...................... 356/338, 341, 343; 250/564, 574

[56] References Cited

U.S. PATENT DOCUMENTS 3,518,437 6/1970 Riggs .............................. 250/574 X
3,843,268 10/1974 Kaye ................................... 356/246
3,936,192 2/1976 Skala ................................ 356/341 X
4,146,799 3/1979 Pitt et al. ............................. 250/574

Primary Examiner—John K. Corbin
Assistant Examiner—Matthew W. Koren
Attorney, Agent, or Firm—Burd, Bartz & Gutenkauf

[57] ABSTRACT

A laser light beam is projected through a fluid measuring cell having a fluid accommodating chamber and inlet and outlet pathways for the fluid. The light is separated into transmitted light and scattered light. Separate light detectors sense the transmitted light and scattered light. An electric control circuit uses the variations of the intensity of the transmitted light to compensate for fluctuations in the intensity of the scattered light to provide an output related to the intensity of the scattered light.

26 Claims, 4 Drawing Figures

LASER LIGHT SCATTERING PHOTOMETER

BACKGROUND AND DETAILED EXPLANATION OF INVENTION

The present invention relates to a laser light scattering photometer for the determination of molecular weight of the solute component in the subjected liquid by detecting the intensity of the scattering light from the liquid. This invention offers equipment for the measurement of the intensity of the scattering light by means of a novel optical system and measuring "cell" structure.

The light scattering method is playing an important role for determining the molecular weight and size of solute-molecule in the solution. This method is not widely used because of the complicated operative techniques for measurement. For instance, it is necessary to extrapolate the concentration and the angle to zero by the Method of the Zim Plot, for example, by measuring the intensity of the scattering light at the angle in the range from 30° to 150° usually as to several samples with different concentrations of the solutions.

In laser light scattering method it is possible to determine the molecular weight without extrapolating technique of both factors as in the above. That is, in the use of laser light scattering photometer, it is possible to measure the intensity of scattering light at a small angle of 5° or lesser angles.

In practice, therefore extrapolation to zero-angle is unnecessary. Futhermore, because of higher intensity of the incident light, very dilute solution can be used as a sample for measurement, thus usually there is no necessity to extrapolate to zero-concentration.

In such a case, the intensity of the scattering light to be measured is proportional to the product of the molecular weight of the solute and the concentration of the solution, therefore, by combined use of laser light scattering photometer as a molecular weight detector with a concentration detector, it is possible to measure the molecular weight of the solute in the subjected solution continuously.

Conventionally known laser light scattering photometers have specific structures especially on the measuring "cell" part, which require special processing acuity, and thus, lacking in practicability. Moreover, the fluctuation of the intensity of the incident light becomes a cause of variation of the intensity of scattering light, thereby, it is difficult to obtain stable measuring values as the dermerit. Then further practical photometers are required.

The present inventors have been making efforts for improving the above defects, and have completed a laser light scattering photometer in featuring the equipment provided with the optical system removing the fluctuation of the itensity of scattered light due to the change of the intensity of the incident light, and its corresponding electronic system as well as the measuring cell with much simpler structure than that of the conventional ones.

In other words, in a laser light scattering photometer for measuring the intensity of scattered light of a subjected testing liquid, a measuring cell and an annular slit equipped with a light trap at the central position are aligned so as to match the axis of the incident beam. A pair of detectors in a receiving optical system monitors the intensity of the light transmitted through the measuring cell and is reflected by the light trap. The second light detector detects the intensity of scattered light at the scattering angle restricted by the annular slit. An electronic circuit eliminates the intensity fluctuation in which the the fluctuation in the intensity of the transmitted light is detected by the detector for transmitted light. The electronic circuit has an output signal corresponding to the fluctuation in intensity of the transmitted light. This output signal is put into the detector for scattered light as input signal. Thus, by the output signal, the fluctuation in the output of the scattered light detector caused by the fluctuation in the intensity of the incident beam is compensated.

The measuring cell is a flow-type cell composed of a cell-composing material having cylindrical beam-passing part perforated to make the central axis matching the axis of a laser incident beam and cylindrically perforated pathway of a testing liquid, connected to the beam-passing part. Two glass blocks are mounted on front and rear faces of the cell-composing material against laser incident beam.

DESCRIPTION OF PREFERRED EMBODIMENTS

The major part of this equipment has a measuring cell 2 and annular slit 4 equipped with light trap 3 at the central position thereof. The light trap 3 is aligned so as to match the axis of the incident beam which is the optical axis of the system. The system includes a pair of detectors receiving scattered light and transmitted light. By measuring the intensity of the elements of transmitted and scattered light, the fluctuation in the intensity of scattered light due to the change of intensity of incident light can be compensated.

Figure 1:
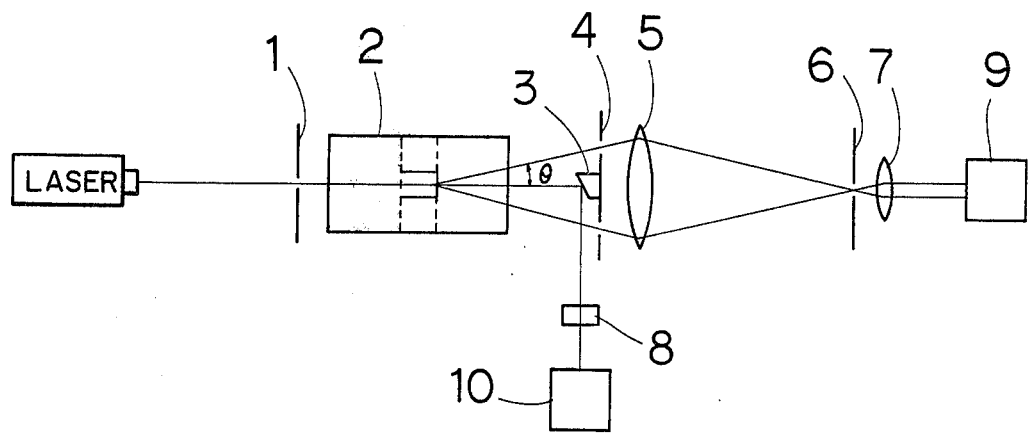
FIG. 1 is a diagrammatic view of an optical system having the fluid measuring cell and photometers of the invention.

As shown in FIG. 1, laser incident light passing through the slit 1 is spectroscopically divided into two elements, namely, the element of scattered light from the testing liquid and the element of transmitted light transmitted through measuring cell 2 having the central axis in conformity with the incident ray axis.

The transmitted light is reflected at the right angles by the light trap 3, attached to the central position of the annular slit 4 whose axis is in accord with the axis of the incident beam light trap 3 has a ray-receiving plane at an angle of 45° against the ray axis of the incident beam. A photomultiplier tube 10 (hereinafter referred to as R-PM) detects the transmitted light reflected by trap 3 through neutral filter 8. The scattered light is converged by the lens 5 after passing through the annular slit 4 whose axis is in accord with the axis of incident beam, corresponding to the specific scattering angle $\theta$.

The light beam after passing through the light-receiving slit 6 becomes a parallel ray by the lens 7 and is received by the photomultiplier tube 9 (hereinafter referred to as S-PM) for detecting the scattered light. The size of annular slit can be selected to make the scattering angle less than 10°. Preferably, the angle is less than 5°.

Figure 2:
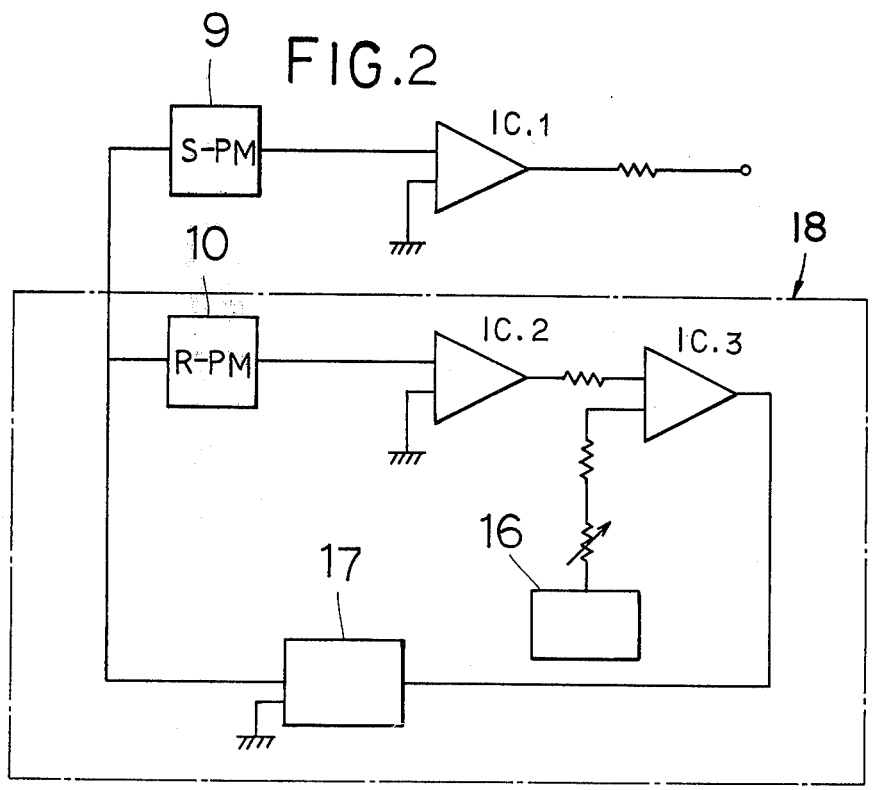
FIG. 2 is a circuit diagram of an electronic control circuit for eliminating the effect of variation of intensity of incident light.

The elements of transmitted light and scattered lights are each detected at two detecting parts of R-PM 10 and S-PM 9 to compensate for the fluctuation of the intensity of the scattered light due to the variations of the intensity of the incident light at the electronic control circuit composed and illustrated in FIG. 2.

The electronic control circuit ensures less fluctuation in the measured values of the intensity of the scattered light and the accuracy of the measurements.

FIG. 2 shows a rough sketch of an example of the electronic control circuit 18 for eliminating the effect of variation of the intensity of incident or scattered light. The control circuit 18 has an amplifier IC 2 connected in series with R-PM 10 and amplifier IC 3. A reference voltage setting part 16 of the photomultiplier tube is connected to amplifier IC 3 in parallel with amplifier IC 2. The output of amplifier IC 3 is fed back to power supply source 17 of the photomultiplier tube. Power supply source 17 is connected to R-PM 10 to complete the fluctuation elimination circuit. The output voltage of power supply source 17 obtained from the fluctuation elimination circuit is the input to S-PM 9. The signal of S-PM 9 is fed to amplifier IC 1. That is, the intensity of the incident light is converted to an electronic signal by R-PM 10. The output signal of R-PM 10 is fed to amplifier IC 3 after amplification by amplifier IC 2. At amplifier IC 3, the input from amplifier IC 2 is compared with the voltage of the reference voltage supplied by the voltage setting part 16 of the photomultiplier tube and for making the difference of them zero. The supplied voltage from power supply source 17 of the photomultiplier tube starts the operation. For instance, when an increasing variation occurs in the intensity of the incident light, and the input from amplifier IC 2 becomes greater than the voltage from voltage setting part 16, the input signal of amplifier 2 is reduced to make the difference of the signals zero. This dissolves the increasing variation of the input from S-PM 9.

Figure 3:
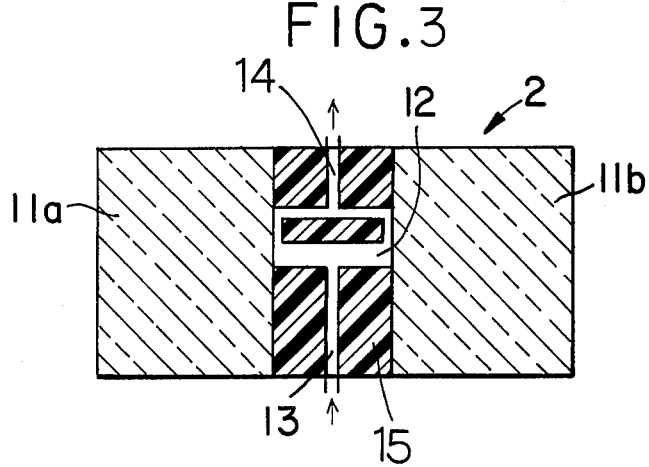
FIG. 3 is a sectional view of a fluid measuring cell used in the system of FIG. 1.
Figure 4:
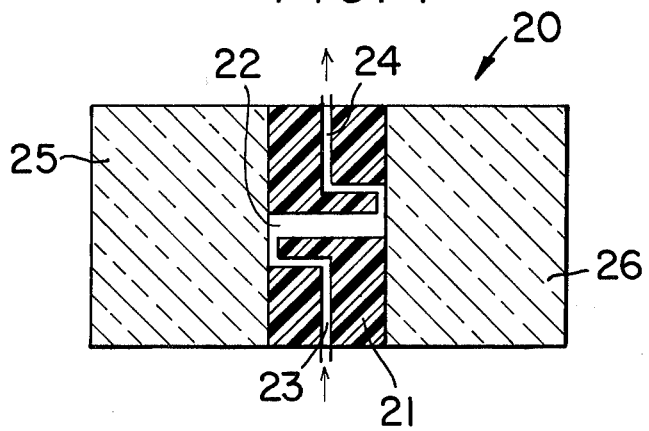
FIG. 4 is a sectional view of a modification of a fluid measuring cell

FIGS. 3 and 4 show examples of the fluid cell 2 in planes parallel to the laser incident light.

The measuring cell 2 in this invention is a flow-type cell composed of two glass blocks 11a and 11b mounted to the front and rear faces of a body 15 of cell-composing material. Body 15 has laser beam passing pathway or chamber 12, an inlet-liquid pathway 13, and outlet-liquid pathway 14 connected to pathway 12. Pathway 12 is a cylindrical liquid testing chamber having a central axis coincident with the ray axis of laser incident beam. A disc 16 in pathway 12 aligned with the axis of pathways 13 and 14 causes the fluid, such as a liquid, to flow outwardly toward the outer portion of the fluid testing chamber. In other words, the fluid in the fluid testing chamber flows around the outer circumferential edge of disc 16 to the outlet pathway 14. The subjected liquid is introduced from the inlet-liquid pathway 13, and passes through the beam-passing pathway 12, then it is sent to flow out of the outlet-liquid pathway 14.

In this case, the incident light passed through the front glass block 11a, central axis of beam-passing pathway 12, and rear glass blocks 11b, thereby spectroscopically dividing the light into two elements, namely, transmitted light and scattered light. The body 15 is made of material having non-light reflecting characteristics. Preferably, the material of body 15 is processed synthetic resins with favorable solvent proof nature, such as black poly-(tetafluoroethylene) or poly-(chlorotrifluoroethylene).

The beam-passing pathway 12, inlet-liquid pathway 13 and outlet-liquid pathway 14 can be easily manufactured by processing the said cell-composing material with cylindrical perforation.

Referring to FIG. 4, there is shown a modification of the measuring cell indicated generally at 20. Measuring cell 20 has a body 21 of light opaque material similar to body 15. The center portion of body 21 has a cylindrical liquid testing chamber or pathway 22 for accommodating the testing of liquid. A right angle inlet pathway 23 extends upwardly into body 21, as shown in FIG. 4, and opens to the right side of chamber 22. An outlet pathway 24 is located in the upper portion of body 15 and is open to the right side of chamber 22. Glass blocks 25 and 26 are mounted to the front and rear surfaces of body 21.

The size of the beam passing pathways 12 and 22 in the fluid flow type measuring cells 2 and 20 is not particularly restricted. Preferably, it is desirable that the diameter of each pathway 2 and 22 of the cylinder be less than 4 mm. In some cases, a diameter of less than 2 mm is preferable. The length of the cylinder of the pathways 12 and 22 is less than 20 mm. Preferably, this length is less than 10 mm. The flow type fluid measuring cells 2 and 22 of the invention have capacities of less than 100 $\mu$l, and usually smaller than 50 $\mu$l. The fluid measuring cells have the merit of being able to make measurement of a minor amount of a sample with high accuracy. Since the material of the cell body is black, it can absorb the reflected light from the surface between the fluid and the glass blocks. This makes possible the measurement of the intensity of scattered light with a low level of stray light. Since the beam passing pathways 12 and 22 have the shape of simple cylinders and small dead volumes, the subjected testing fluid does not have a detracting flow disorder. Therefore, this equipment is particularly superior as a detecting device of successively eluted components discharged from the molecular weight fractionating equipments such as GPC or FFF, etc. as mentioned later.

This flow type laser light scattering photometer of the invention measures the intensity of the scattered light of a subjected test fluid with high accuracy. The photometer is useable as a detector of fractionating equipments such as Gel-Permeation Chromatograph (GPC) of Field-Flow Fractionation (FFF). This equipment using the photometer of the invention is operable to make direct evaluation of the molecular weight of each effluent of the subjected liquid. This equipment is also operable to provide analytic function of molecular weight to the fractionating function by GPC.

Stable measurement values were obtained in a test for the stability of the response corresponding to the intensity of scattered light from tetra-hydrofuran (THF). The extent of fluctuation of the base line had a variation of less than 0.1% after continuous measurement for 24 hours. This measurement was compared with a photometer without operating the fluctuation elimination circuit, as shown in FIG. 2. The result of this test was that the variation of the base line was 4%.

What we claim is:
1. An apparatus for measuring the intensity of light scattered by a test fluid comprising: means for providing a light beam, measuring cell means having a chamber for accommodating test fluid, said chamber of the measuring cell means being aligned with the optical axis of the light beam whereby the light beam passes through the test fluid as transmitted light and scattered light, means having an annular slit located adjacent the measuring cell means aligned to match the axis of the scattered light, first light detector means operable to monitor the intensity of scattered light passing through said annular slit, second light detector means operable to monitor the intensity of the transmitted light, and electronic circuit means connected to said first and second light detector means operable to use variations of the intensity of the transmitted light to compensate for fluctuations of the intensity of the scattered light to provide an output related to the intensity of the scattered light, said electronic circuit means includes first amplifier means connected to the output of the second light detector means, second amplifier means connected to the output of the first amplifier means, reference voltage means connected to the second amplifier means providing the second amplifier means with a reference voltage, and power supply means connected to the output of the second amplifier means, said power supply means having an output related to the output of the second amplifier means and connected to the input of the first light detector means whereby variations of the scattered light are compensated by the variations of the transmitted light detected by the second light detector means.

2. The apparatus of claim 1 wherein: said measuring cell means includes an inlet pathway connected to the chamber for carrying test fluid to the chamber, and an outlet pathway connected to the chamber for carrying test fluid from the chamber whereby said test fluid flows through said chamber.

3. The apparatus of claim 2 wherein: the measuring cell means includes a portion made of non-light reflecting material, said portion having said inlet pathway and outlet pathway.

4. The apparatus of claim 1 wherein: the measuring cell means includes a body having a central chamber, an inlet pathway open to one side of the chamber, and an outlet pathway open to the other side of the chamber, said chamber and inlet and outlet pathways accommodating flowing test fluid, and glass block means secured to opposite sides of the body.

5. The apparatus of claim 4 wherein: said body is made of non-light reflecting material.

6. The apparatus of claim 1 wherein: the first light detector means comprises a photomultiplier tube.

7. The apparatus of claims 1 or 6 wherein: the second light detector means comprises a photomultiplier tube.

8. The apparatus of claims 1 or 6 wherein: the second light detector means comprises a photomultiplier tube.

9. The apparatus of claim 1 including: lens means between the means having an annular slit and the first light means for directing the scattered light to the first light detector means.

10. The apparatus of claim 1 including: means located along the optical axis of the light beam between the measuring cell means and means having an annular slit to reflect the transmitted light to the second light detector means.

11. The apparatus of claim 10 wherein: the means to reflect the transmitted light to the second light detector means is secured to means having the annular slit.

12. An apparatus for measuring the intensity of light scattered by a test fluid comprising: means for providing a light beam, measuring cell means having a chamber accommodating test fluid, said measuring cell means including a body of non-light reflecting material having a central chamber, an inlet pathway open to one side of the chamber, and an outlet pathway open to the other side of said chamber, said chamber and inlet and outlet pathways accommodating flowing test fluid, glass block means secured to opposite sides of the body, said chamber being aligned with the optical axis of the light beam whereby the light beam passes through the test fluid in said chamber as transmitted light and scattered light, means having an annular slit located adjacent the measuring cell means aligned to match the axis of the scattered light, first light detector means operable to monitor the intensity of scattered light passing through said annular slit, second light detector means operable to monitor the intensity of the transmitted light, and electronic circuit means connected to said first and second light detector means operable to use variations of the intensity of the transmitted light to compensate for fluctuations of the intensity of the scattered light to provide an output related to the intensity of the scattered light, said circuit means having first means connected to the output of the second light detector means, reference voltage means connected to the first means, and power supply means connected to the output of the first means and the input of the first light detector means whereby variations of the scattered light are compensated by the variations of the transmitted light detected by the second light detector means.

13. The apparatus of claim 12 wherein: the first light detector means comprises a photomultiplier tube.

14. The apparatus of claim 12 including: lens means between the means having an annular slit and the first light detector means for directing the scattered light to the first light detector means.

15. The apparatus of claim 12 wherein: said first means of the electronic circuit means includes first amplifier means connected to the output of the second light detector means, and second amplifier means connected to the output of the first amplifier means, said reference voltage means being connected to the second amplifier means providing the second amplifier means with a reference voltage, and said power supply means being connected to the output of the second amplifier means, said power supply means having an output related to the output of the second amplifier means and connected to the input of the first light detector means.

16. The apparatus of claim 12 including: means located along the optical axis of the light beam between the measuring cell means and means having an annular slit to reflect the transmitted light to the second light detector means.

17. The apparatus of claim 16 wherein: the means to reflect the transmitted light to the second light detector means is secured to means having the annular slit.

18. The apparatus of claim 12 wherein: said first means of the electronic circuit means includes amplifier means connected to the output of the second light detector means, said reference voltage means being connected to the amplifier means providing the amplifier means with a reference voltage, and said power supply means being connected to the amplifier means, said power supply means having an output related to the output of the amplifier means and connected to the input of the first light detector means.

19. An apparatus for measuring the intensity of light scattered by a test fluid comprising: means for providing a light beam, measuring cell means having a chamber for accommodating test fluid, said chamber of the measuring cell means being aligned with the optical axis of the light beam whereby the light beam passes through the test fluid as transmitted light and scattered light, means having a slit located adjacent the measuring cell means aligned to match the axis of the scattered light, first light detector means operable to monitor the intensity of scattered light passing through said slit, second light detector means operable to monitor the intensity of the transmitted light, and electronic circuit means connected to said first and second light detector means operable to use variations of the intensity of the transmitted light to compensate for fluctuations of the intensity of the scattered light to provide an output related to the intensity of the scattered light, said electronic circuit means having amplifier means connected to the output of the second light detector means, reference voltage means connected to said amplifier means providing said amplifier means with a reference voltage, and power supply means connected to the output of said amplifier means and input of the first light detector means whereby variations of the scattered light are compensated by the variations of the transmitted light detected by the second light detector means.

20. The apparatus of claim 19 wherein: said measuring cell means includes a body of non-light reflecting material, said body having said chamber, an inlet pathway connected to the chamber for carrying test fluid to the chamber, and an outlet pathway connected to the chamber for carrying test fluid from the chamber whereby said test fluid flows through said chamber.

21. The apparatus of claim 20 including: glass block means secured to opposite sides of the body.

22. The apparatus of claim 19 wherein: the first light detector means comprises a photomultiplier tube.

23. The apparatus of claims 19 or 22 wherein: the second light detector means comprises a photomultiplier tube.

24. The apparatus of claim 19 including: lens means between the means having a slit and the first light detector means for directing the scattered light to the first light detector means.

25. The apparatus of claim 19 including: means located along the optical axis of the light beam between the measuring cell means and means having a slit to reflect the transmitted light to the second light detector means.

26. The apparatus of claim 25 wherein: the means to reflect the transmitted light to the second light detector means is secured to means having the slit.

* * * * *